United States Patent
Takahashi et al.

(10) Patent No.: US 10,471,044 B2
(45) Date of Patent: **\*Nov. 12, 2019**

(54) POST NERVE INJURY REHABILITATION EFFECT-ENHANCING AGENT COMPRISING ALKYL ETHER DERIVATIVE OR SALT THEREOF

(71) Applicant: FUJIFILM Toyama Chemical Co., Ltd., Chuo-ku (JP)

(72) Inventors: Takuya Takahashi, Yokohama (JP); Tomohiro Okuda, Toyama (JP)

(73) Assignee: FUJIFILM Toyama Chemical Co., Ltd., Chuo-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/005,774

(22) Filed: Jun. 12, 2018

(65) Prior Publication Data

US 2018/0289668 A1    Oct. 11, 2018

Related U.S. Application Data

(63) Continuation of application No. 15/115,416, filed as application No. PCT/JP2015/052617 on Jan. 30, 2015, now Pat. No. 10,039,744.

(30) Foreign Application Priority Data

Jan. 31, 2014 (JP) .................. 2014-017587

(51) Int. Cl.
    *A61K 31/397* (2006.01)
(52) U.S. Cl.
    CPC .................. *A61K 31/397* (2013.01)
(58) Field of Classification Search
    CPC .................................. A61K 31/397
    USPC .................................. 514/210.19
    See application file for complete search history.

(56) References Cited

U.S. PATENT DOCUMENTS

| | | | |
|---|---|---|---|
| 8,119,625 B2 | 2/2012 | Iwakami | |
| 10,039,744 B2 * | 8/2018 | Takahashi | A61K 31/397 |
| 2005/0070521 A1 | 3/2005 | Saitoh et al. | |
| 2005/0186545 A1 | 8/2005 | Okano et al. | |
| 2009/0069576 A1 | 3/2009 | Saitoh et al. | |
| 2009/0093453 A1 | 4/2009 | Iwakami et al. | |

FOREIGN PATENT DOCUMENTS

| | | | |
|---|---|---|---|
| EP | 1 514 542 A1 | 3/2005 | |
| EP | 1 614 419 A1 | 1/2006 | |
| EP | 2 011 796 A1 | 1/2009 | |
| JP | 2013-177410 A | 9/2013 | |
| JP | 2013177410 * | 9/2013 | A61K 47/36 |
| RU | 2 397 169 C2 | 8/2010 | |
| WO | 03/035647 A1 | 5/2003 | |
| WO | 03/045137 A1 | 6/2003 | |
| WO | WO 2003/045137 * | 6/2003 | A61K 47/36 |
| WO | 2007/125913 A1 | 11/2007 | |

OTHER PUBLICATIONS

Fukushima et al. Neurochem Int. 2006, 48 (2) , 124-30.*
Fukushima et al. Biochemical and Biophysical Research Communications, (2011), 407(4), 730-734.*
Mossberg J Head Trauma Rehabil. May-Jun. 2010;25(3):173-83.*
Weightman J Head Trauma Rehabil. May-Jun. 2010;25(3):206-18.*
Marriott, Pharmaceutical Compound and Dispensing, Second Edition, 2010, 1-288.*
Ansel, Pharmaceutical Dosage Forms and Drug Delivery Systems, 1999.*
Tetsuo Fukushima et al., "T-817MA, a novel neurotrophic agent, improves sodium nitroprusside-induced mitochondrial dysfunction in cortical neurons", Neurochemistry International, 2006, vol. 48, pp. 124-130.
Neha Lohda et al., "Increased Force Variability in Chronic Stroke: Contributions of Force Modulation below 1 Hz", Plos One, Dec. 2013, vol. 8, Issue 12, pp. 1-9.
Marie-Helene Milot et al., "A crossover pilot study evaluating the functional outcomes of two different types of robotic movement training in chronic stroke survivors using the arm exoskeleton Bones", Journal of Neuroengineering and Rehabilitation, 2013, vol. 10, pp. 1-12.
International Search Report dated Apr. 21, 2015 in PCT/JP2015/052617 filed Jan. 30, 2015.
Extended European Search Report dated Jul. 31, 2017 in Patent Application No. 15743367.3.
Combined Office Action and Search Report dated Aug. 30, 2018 in Russian Patent Application No. 2016135236/15 (with English translation), citing references AO-AQ and AX-AZ therein, 23 pages.

(Continued)

*Primary Examiner* — Nizal S Chandrakumar
(74) *Attorney, Agent, or Firm* — Oblon, McClelland, Maier & Neustadt, L.L.P.

(57) ABSTRACT

Provided is a medicinal composition characterized by comprising an alkyl ether derivative represented by general formula [1]

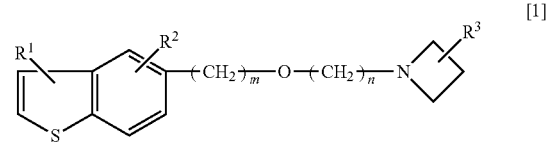

[wherein: $R^1$ and $R^2$ are the same or different and represent a hydrogen atom, a halogen atom, an optionally substituted $C_{1-6}$ alkyl group, an optionally substituted aryl group, etc.; $R^3$ represents an optionally protected hydroxyl group, etc.; and m and n are the same or different and represent an integer of 1 to 6] or a salt thereof. The medicinal composition according to the present invention is useful as a post nerve injury rehabilitation effect-enhancing agent.

13 Claims, 3 Drawing Sheets

(56) References Cited

OTHER PUBLICATIONS

Hirata, K. et al., "A Novel Neurotrophic Agent, T-817MA [1-(3-[2-(1-Benzothiophen-5-yl) Ethoxy] Propyl)-3-azetidinol Maleate], Attenuates Amyloid-β-Induced Neurotoxicity and Promotes Neurite Outgrowth in Rat Cultured Central Nervous System Neurons", The Journal of Pharmacology and Experimental Therapeutics, 2005, pp. 252-259.
Kharkyevitch, D. A., "Pharmacology",Meditsina, 1987, 9 pages (with English translation).
Byelikov, V. G., "Pharmaceutical Chemistry", M. Higher Education, 1993, 17 pages.
Office Action dated Nov. 23, 2018 in European Patent Application No. 15 743 367.3.
Conroy, B. et al. "An Exploration of Central Nervous System Medication Use and Outcomes in Stroke Rehabilitation", Archives of Physical Medicine and Rehabilita, W. B. Saunders, United States, XP005210372, vol. 86, No. 12, Dec. 1, 2005, pp. 73-81.

\* cited by examiner

POST NERVE INJURY REHABILITATION EFFECT-ENHANCING AGENT COMPRISING ALKYL ETHER DERIVATIVE OR SALT THEREOF

CROSS-REFERENCES TO RELATED APPLICATIONS

This application is a continuation of U.S. patent application Ser. No. 15/115,416, filed Jul. 29, 2016, which is the National Stage of the International Patent Application No. PCT/JP2015/052617, filed Jan. 30, 2015, the disclosures of which are incorporated herein by reference in their entireties. This application claims priority to Japanese Application No. 2014-017587, filed Jan. 31, 2014.

TECHNICAL FIELD

The present invention relates to an excellent post-nerve injury rehabilitation effect-enhancing agent containing an alkyl ether derivative or a salt thereof.

BACKGROUND ART

When central nerve tissue such as the brain or spinal cord is injured, the higher function controlled by the injured nerves is impaired. The number of patients with stroke, which is a typical example of nerve injury, is as high as about 1,300,000 in Japan, which leads to a serious social loss.

When nerve injury such as stroke or spinal cord injury has occurred, rehabilitation for the purpose of recovering from functional disorders is recommended. However, the effect of recovery from the functional disorders obtained with rehabilitation is insufficient, and many cases have been reported where the disorders remain, or returning to society is not possible, even after rehabilitation. The effect of recovery from functional disorders obtained with conventional rehabilitation is therefore limited (Non Patent Documents 1 and 2).

The alkyl ether derivatives described in Patent Documents 1 and 2 have been known thus far to have neuroprotection action, neuroregeneration action, neurite outgrowth-promoting action, and neurogenesis-inducing action (Patent Documents 1 and 2).

PRIOR ART DOCUMENTS

Patent Document

Patent Document 1: WO 03/035647
Patent Document 2: WO 2007/125913

Non Patent Document

Non Patent Document 1: Plos One, Vol. 8, Issue 12, e83468 (2013)
Non Patent Document 2: Journal of Neuroengineering and Rehabilitation, Vol. 10, Pages 112-123 (2013)

SUMMARY OF INVENTION

Technical Problem

A compound which has the action of enhancing a post-nerve injury rehabilitation effect, and is useful as a post-nerve injury rehabilitation effect-enhancing agent is required.

Solution to Problem

Under such circumstances, the present inventors found that an alkyl ether derivative represented by the following general formula [1]:

[1]

or a salt thereof, wherein $R^1$ and $R^2$ are the same or different, and each represent one or more groups selected from a hydrogen atom, a halogen atom, an optionally substituted $C_{1-6}$ alkyl group, an optionally substituted aryl group, an optionally substituted ar-$C_{1-6}$ alkyl group, an optionally substituted $C_{1-6}$ alkoxy group, an optionally substituted aryloxy group, an optionally substituted $C_{1-6}$ alkylthio group, an optionally substituted arylthio group, an optionally substituted $C_{2-6}$ alkenyl group, an optionally substituted $C_{2-6}$ alkenyloxy group, an optionally substituted $C_{1-6}$ alkylamino group, an optionally substituted $C_{1-6}$ alkylsulfonyl group, an optionally substituted arylsulfonyl group, an optionally substituted carbamoyl group, an optionally substituted heterocyclic group, an optionally protected amino group, an optionally protected hydroxyl group, an optionally protected carboxyl group, a nitro group and an oxo group; $R^3$ represents an optionally substituted $C_{1-6}$ alkylamino group, an optionally protected amino group or an optionally protected hydroxyl group; and m and n are the same or different, and each represent an integer from 1 to 6, has the action of enhancing the effect of recovery from functional disorders obtained with post-nerve injury rehabilitation, and is therefore useful as a post-nerve injury rehabilitation effect-enhancing agent, thereby accomplishing the present invention.

According to the present invention, the following inventions are provided.

(1) A post-nerve injury rehabilitation effect-enhancing agent containing the alkyl ether derivative represented by the general formula [1] or a salt thereof.

(2) The post-nerve injury rehabilitation effect-enhancing agent according to (1), containing the alkyl ether derivative or a salt thereof, wherein $R^1$ and $R^2$ are the same or different, and are each a hydrogen atom, a halogen atom or a $C_{1-6}$ alkoxy group.

(3) The post-nerve injury rehabilitation effect-enhancing agent according to (1) or (2), containing the alkyl ether derivative or a salt thereof, wherein m is 2; and n is 2 or 3.

(4) The post-nerve injury rehabilitation effect-enhancing agent according to any one of (1) to (3), containing the alkyl ether derivative or a salt thereof, wherein $R^3$ is an optionally protected hydroxyl group.

(5) The post-nerve injury rehabilitation effect-enhancing agent according to (1), wherein the alkyl ether derivative is 1-(3-(2-(1-benzothiophen-5-yl)ethoxy)propyl)azetidin-3-ol.

(6) A functional disorder recovery-enhancing agent and/or a functional disorder alleviation-enhancing agent for a patient with nerve injury to undergo rehabilitation, containing the alkyl ether derivative represented by the general formula [1] or a salt thereof.

(7) The functional disorder recovery-enhancing agent and/or the functional disorder alleviation-enhancing agent for a patient with nerve injury to undergo rehabilitation according to (6), containing the alkyl ether derivative or a salt thereof, wherein $R^1$ and $R^2$ are the same or different, and are each a hydrogen atom, a halogen atom or a $C_{1-6}$ alkoxy group.

(8) The functional disorder recovery-enhancing agent and/or the functional disorder alleviation-enhancing agent for a patient with nerve injury to undergo rehabilitation according to (6) or (7), containing the alkyl ether derivative or a salt thereof, wherein m is 2; and n is 2 or 3.

(9) The functional disorder recovery-enhancing agent and/or the functional disorder alleviation-enhancing agent for a patient with nerve injury to undergo rehabilitation according to any one of (6) to (8), containing the alkyl ether derivative or a salt thereof, wherein $R^3$ is an optionally protected hydroxyl group.

(10) The functional disorder recovery-enhancing agent and/or the functional disorder alleviation-enhancing agent for a patient with nerve injury to undergo rehabilitation according to (6), wherein the alkyl ether derivative is 1-(3-(2-(1-benzothiophen-5-yl)ethoxy)propyl)azetidin-3-ol.

According to the present invention, the following inventions are also provided.

(a) A post-stroke, post-brain injury or post-spinal cord injury rehabilitation effect-enhancing agent containing the alkyl ether derivative represented by the general formula [1] or a salt thereof.

(b) A functional disorder recovery-enhancing agent and/or a functional disorder alleviation-enhancing agent for a patient with stroke, a patient with brain injury or a patient with spinal cord injury to undergo rehabilitation, containing the alkyl ether derivative represented by the general formula [1] or a salt thereof.

(c) Use of the alkyl ether derivative represented by the general formula [1] or a salt thereof, in the manufacture of a medicament for enhancing a post-nerve injury rehabilitation effect.

(d) Use of the alkyl ether derivative represented by the general formula [1] or a salt thereof, in the manufacture of a medicament for treating a disease against which the post-nerve injury rehabilitation effect-enhancing agent shows efficacy.

(e) Use according to (c) or (d), wherein the nerve injury is stroke, brain injury or spinal cord injury.

(f) A method for use in the treatment of a disease against which the post-nerve injury rehabilitation effect-enhancing agent shows efficacy, including the step of administering to a subject (a mammal including a human) an effective amount of treatment of the alkyl ether derivative represented by the general formula [1] or a salt thereof.

(g) A method for enhancing a post-nerve injury rehabilitation effect, including the step of administering to a subject (a mammal including a human) the alkyl ether derivative represented by the general formula [1] or a salt thereof.

(h) The method according to (f) or (g), wherein the nerve injury is stroke, brain injury or spinal cord injury Advantageous Effects of Invention The alkyl ether derivative represented by the general formula [1] or a salt thereof according to the present invention has the action of enhancing the post-nerve injury rehabilitation effect, and is useful as a post-nerve injury rehabilitation effect-enhancing agent.

DESCRIPTION OF EMBODIMENTS

The present invention will be hereinafter described in detail.

The terms used in the present specification have the following meanings, unless otherwise specified.

The "treatment" means prevention or therapy.

The "treatment agent" means a substance provided for preventive or therapeutic purposes.

The "halogen atom" means a fluorine atom, a chlorine atom, a bromine atom or an iodine atom.

The "$C_{1-6}$ alkyl group" means a straight or branched $C_{1-6}$ alkyl group such as a methyl, ethyl, propyl, isopropyl, butyl, isobutyl, tert-butyl, pentyl or hexyl group.

The "$C_{2-6}$ alkenyl group" means a $C_{2-6}$ alkenyl group such as vinyl, propenyl, butenyl, pentenyl or hexenyl.

The "acyl-$C_{1-6}$ alkyl group" means an acyl-$C_{1-6}$ alkyl group such as, for example, acetylmethyl, benzoylmethyl, p-nitrobenzoylmethyl, p-bromobenzoylmethyl, p-methoxybenzoylmethyl or 1-benzoylethyl.

The "acyloxy-$C_{1-6}$ alkyl group" means an acyloxy-$C_{1-6}$ alkyl group such as, for example, acetoxymethyl, propionyloxymethyl or pivaloyloxymethyl.

The "arylthio-$C_{1-6}$ alkyl group" means a group such as, for example, phenylsulfenylmethyl or 2-(p-nitrophenylsulfenyl)ethyl.

The "arylsulfonyl-$C_{1-6}$ alkyl group" means an aryl sulfonyl-$C_{1-6}$ alkyl group such as, for example, p-toluenesulfonylethyl.

The "nitrogen-containing heterocyclic $C_{1-6}$ alkyl group" means a nitrogen-containing heterocyclic $C_{1-6}$ alkyl group such as, for example, phthalimidomethyl or succinimidomethyl.

The "$C_{3-8}$ cycloalkyl group" means a $C_{3-8}$ cycloalkyl group such as, for example, cyclopropyl, cyclobutyl, cyclopentyl or cyclohexyl.

The "$C_{1-6}$-alkylthio-$C_{1-6}$ alkyl group" means a $C_{1-6}$-alkylthio-$C_{1-6}$ alkyl group such as, for example, methylthiomethyl, ethylthiomethyl or propylthiomethyl.

The "$C_{1-6}$-alkoxy-$C_{1-6}$ alkyl group" means a $C_{1-6}$-alkyloxy-$C_{1-6}$ alkyl group such as, for example, methoxymethyl or 1-ethoxyethyl.

The "ar-$C_{1-6}$-alkyloxy-$C_{1-6}$ alkyl group" means an ar-$C_{1-6}$-alkyloxy-$C_{1-6}$ alkyl group such as, for example, benzyloxymethyl or phenethyloxymethyl.

The "$C_{1-6}$ alkoxy group" means a straight or branched $C_{1-6}$ alkyloxy group such as a methoxy, ethoxy, propoxy, isopropoxy, butoxy, isobutoxy, tert-butoxy, pentyloxy or hexyloxy group.

The "$C_{2-6}$ alkenyloxy group" means a $C_{2-6}$ alkenyloxy group such as a vinyloxy, propenyloxy, butenyloxy, pentenyloxy or hexenyloxy group.

The "$C_{1-6}$ alkylthio group" means a $C_{1-6}$ alkylthio group such as methylthio, ethylthio, propylthio, isopropylthio, butylthio, isobutylthio, tert-butylthio, pentylthio or hexylthio.

The "aryl group" means a phenyl, naphthyl, indanyl or indenyl group.

The "aryloxy group" means a phenyloxy, naphthyloxy, indanyloxy or indenyloxy group.

The "ar-$C_{1-6}$ alkyl group" means an ar-$C_{1-6}$ alkyl group such as a benzyl, diphenylmethyl, trityl or phenethyl group.

The "arylthio group" means a phenylthio, naphthylthio, indanylthio or indenylthio group.

The "acyl group" means a formyl group, a $C_{2-6}$ alkanoyl group such as acetyl, isovaleryl, propionyl or pivaloyl, an ar-$C_{1-6}$-alkylcarbonyl group such as benzylcarbonyl, or an aroyl group such as benzoyl or naphthoyl.

The "$C_{1-6}$ alkyloxycarbonyl group" means a straight or branched $C_{1-6}$ alkyloxycarbonyl group such as, for example, methoxycarbonyl, ethoxycarbonyl, 1,1-dimethylpropoxycarbonyl, isopropoxycarbonyl, 2-ethylhexyloxycarbonyl, tert-butoxycarbonyl or tert-pentyloxycarbonyl.

The "ar-$C_{1-6}$-alkyloxycarbonyl group" means an ar-$C_{1-6}$-alkyloxycarbonyl group such as, for example, a benzyloxycarbonyl or phenethyloxycarbonyl group.

The "aryloxycarbonyl group" means a group such as, for example, phenyloxycarbonyl.

The "heterocyclic oxycarbonyl group" means a group such as, for example, 2-furfuryloxycarbonyl or 8-quinolyloxycarbonyl.

The "$C_{1-6}$ alkylsulfonyl group" means a $C_{1-6}$ alkylsulfonyl group such as, for example, methylsulfonyl, ethylsulfonyl or propylsulfonyl.

The "arylsulfonyl group" means a phenylsulfonyl, p-toluenesulfonyl or naphthyl sulfonyl group.

The "$C_{1-6}$ alkylamino group" means a mono- or di-$C_{1-6}$ alkylamino group such as methylamino, ethylamino, propylamino, isopropylamino, butylamino, dimethylamino, diethylamino, diisopropylamino or dibutylamino.

The "heterocyclic group" means a 5-membered or 6-membered ring, fused ring or bridged ring heterocyclic group containing at least one heteroatom selected from nitrogen, oxygen and sulfur atoms, such as pyrrolidinyl, piperidinyl, piperazinyl, homopiperazinyl, homopiperidinyl, morpholyl, thiomorpholyl, tetrahydroquinolinyl, tetrahydroisoquinolyl, quinuclidinyl, imidazolinyl, pyrrolyl, imidazolyl, pyrazolyl, pyridyl, pyrimidyl, quinolyl, quinolizinyl, thiazolyl, tetrazolyl, thiadiazolyl, pyrrolinyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzisoxazolyl, benzothiazolyl, quinoxalyl, dihydroquinoxalyl, 2,3-dihydrobenzothienyl, 2,3-dihydrobenzopyrrolyl, 2,3-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxonyl or 1,4-benzodioxanyl group.

The "oxygen-containing heterocyclic group" means a group such as, for example, 2-tetrahydropyranyl or 2-tetrahydrofuranyl.

The "sulfur-containing heterocyclic group" means a group such as, for example, tetrahydrothiopyranyl.

The "substituted silyl group" means a group such as, for example, trimethylsilyl, triethylsilyl or tributylsilyl.

The "$C_{1-6}$-alkylsilyl-$C_{1-6}$ alkyl group" means a group such as, for example, 2-(trimethylsilyl)ethyl.

Amino protecting groups include all groups that can be used as general protecting groups for amino groups, for example, those groups described in W. Greene et al., Protective Groups in Organic Synthesis, 4th Edition, Pages 696-868, 2007: John Wiley & Sons, INC. Specific examples include an acyl group, a $C_{1-6}$ alkyloxycarbonyl group, an ar-$C_{1-6}$-alkyloxycarbonyl group, an aryloxycarbonyl group, an ar-$C_{1-6}$-alkyl group, a $C_{1-6}$-alkoxy-$C_{1-6}$ alkyl group, an ar-$C_{1-6}$-alkyloxy-$C_{1-6}$ alkyl group, an arylthio group, a $C_{1-6}$ alkylsulfonyl group, an arylsulfonyl group and a substituted silyl group.

Hydroxyl protecting groups include all groups that can be used as general protecting groups for hydroxyl groups, for example, those groups described in W. Greene et al., Protective Groups in Organic Synthesis, 4th Edition, Pages 16-299, 2007: John Wiley & Sons, Inc. Specific examples include an acyl group, a $C_{1-6}$ alkyloxycarbonyl group, an ar-$C_{1-6}$-alkyloxycarbonyl group, a heterocyclic oxycarbonyl group, a $C_{1-6}$ alkyl group, a $C_{2-6}$ alkenyl group, an ar-$C_{1-6}$ alkyl group, an oxygen-containing heterocyclic group, a sulfur-containing heterocyclic group, a $C_{1-6}$-alkoxy-$C_{1-6}$ alkyl group, an ar-$C_{1-6}$-alkyloxy-$C_{1-6}$ alkyl group, a $C_{1-6}$ alkylsulfonyl group, an arylsulfonyl group and a substituted silyl group.

Carboxyl protecting groups include all groups that can be used as general protecting groups for carboxyl groups, for example, those groups described in W. Greene et al., Protective Groups in Organic Synthesis, 4th Edition, Pages 533-643, 2007: John Wiley & Sons, Inc. Specific examples include a $C_{1-6}$ alkyl group, a $C_{2-6}$ alkenyl group, an aryl group, an ar-$C_{1-6}$ alkyl group, an acyl-$C_{1-6}$ alkyl group, an arylthio-$C_{1-6}$ alkyl group, an arylsulfonyl-$C_{1-6}$ alkyl group, an oxygen-containing heterocyclic group, a $C_{1-6}$-alkylsilyl-$C_{1-6}$ alkyl group, an acyloxy-$C_{1-6}$ alkyl group, a nitrogen-containing heterocyclic $C_{1-6}$ alkyl group, a $C_{3-8}$ cycloalkyl group, a $C_{1-6}$-alkoxy-$C_{1-6}$ alkyl group, an ar-$C_{1-6}$-alkyloxy-$C_{1-6}$ alkyl group, a $C_{1-6}$-alkylthio-$C_{1-6}$ alkyl group and a substituted silyl group.

Examples of substituents for the $C_{1-6}$ alkyl group, the aryl group, the ar-$C_{1-6}$ alkyl group, the $C_{1-6}$ alkoxy group, the aryloxy group, the $C_{1-6}$ alkylthio group, the arylthio group, the $C_{2-6}$ alkenyl group, the $C_{2-6}$ alkenyloxy group, the $C_{1-6}$ alkylamino group, the $C_{1-6}$ alkylsulfonyl group, the arylsulfonyl group, the carbamoyl group and the heterocyclic group on $R^1$ and $R^2$, as well as substituents for the $C_{1-6}$ alkylamino group on $R^3$, include groups selected from a halogen atom, a $C_{1-6}$ alkyl group, a $C_{3-8}$ cycloalkyl group, an aryl group, a $C_{1-6}$ alkoxy group, an aryloxy group, a $C_{1-6}$ alkylthio group, an arylthio group, a $C_{2-6}$ alkenyl group, a $C_{1-6}$ alkylsulfonyl group, an arylsulfonyl group, a $C_{1-6}$ alkylamino group, an optionally protected amino group, an optionally protected hydroxyl group, an optionally protected carboxyl group, an acyl group, a heterocyclic group and the like.

Examples of salts of the compound represented by the general formula [1] include generally known salts with basic groups such as amino groups, or acidic groups such as hydroxyl or carboxyl groups.

Salts with basic groups include, for example, salts with mineral acids such as hydrochloric acid, hydrobromic acid, nitric acid and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid and trifluoroacetic acid; and salts with sulfonic acids such as methanesulfonic acid, benzenesulfonic acid, p-toluenesulfonic acid, mesitylenesulfonic acid and naphthalenesulfonic acid.

Salts with acidic groups include, for example, salts with alkali metals such as sodium and potassium; salts with alkaline earth metals such as calcium and magnesium; ammonium salt; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Among the salts described above, examples of preferable salts include pharmacologically acceptable salts, and an example of a more preferable salt is maleic acid.

Where isomers (for example, optical isomers, geometrical isomers, and tautomers) are present in the alkyl ether derivative represented by the general formula [1] or a salt thereof, the present invention encompasses all the isomers, and also encompasses hydrates, solvates and all crystal forms thereof.

Compounds preferable as the alkyl ether derivative represented by the general formula [1] or a salt thereof used in the present invention include the following compounds.

A compound wherein $R^1$ is a hydrogen atom, a halogen atom or a $C_{1-6}$ alkoxy group is preferable, and a compound wherein $R^1$ is a hydrogen atom is more preferable.

A compound wherein $R^2$ is a hydrogen atom, a halogen atom or a $C_{1-6}$ alkoxy group is preferable, and a compound wherein $R^2$ is a hydrogen atom is more preferable.

A compound wherein $R^3$ is an optionally protected hydroxyl group is preferable, and a compound wherein $R^3$ is a hydroxyl group is more preferable.

A compound wherein m is 2 and n is 2 or 3 is preferable, and a compound wherein m is 2 and n is 3 is more preferable.

The alkyl ether derivative represented by the general formula [1] is particularly preferably 1-(3-(2-(1-benzothiophen-5-yl)ethoxy)propyl)azetidin-3-ol.

The alkyl ether derivative represented by the general formula [1] or a salt thereof according to the present invention has the action of enhancing the post-nerve injury rehabilitation effect, and a pharmaceutical composition containing the alkyl ether derivative represented by the general formula [1] or a salt thereof is useful for the treatment of a disease against which the post-nerve injury rehabilitation effect-enhancing agent shows efficacy.

A method in which the alkyl ether derivative represented by the general formula [1] or a salt thereof according to the present invention is administered is useful as a method for treating a disease against which the post-nerve injury rehabilitation effect-enhancing agent according to the present invention shows efficacy.

The "post-nerve injury rehabilitation" is intended to reduce the duration of hospitalization after nerve injury, achieve self-reliance in self-care at an early stage and improve the QOL (Quality of Life), and means the course of training performed to achieve recovery of a functional disorder caused by nerve injury at an earlier stage and/or alleviate the functional disorder (for example, to achieve recovery of the function close to the functional level before the nerve injury).

The post-nerve injury rehabilitation is performed, for example, in the acute phase, convalescent phase, and/or maintenance phase, depending on the post-nerve injury period and the condition of the patient. Specific examples include motor dysfunction recovery training such as muscle strength augmentation, joint-motion-range training for the fingers, knees and the like, as well as movement training such as walking; language dysfunction recovery training; and/or cognitive dysfunction recovery training. A preferable example is motor dysfunction recovery training.

The "rehabilitation effect" means the recovery and/or alleviation of a functional disorder through rehabilitation.

The "functional disorder" to be recovered and/or alleviated by rehabilitation means a functional disorder caused by nerve injury. Specific examples include motor dysfunction, sensory dysfunction and language dysfunction. Preferable examples include motor dysfunction and language dysfunction, and a more preferable example is motor dysfunction. An even more preferable example is motor dysfunction of limbs. Note, however, that mental dysfunction such as depressive symptoms and cognitive dysfunction such as dementia are not included.

The "rehabilitation effect-enhancing" means inducing greater extent of the recovery from functional disorder and/or promoting alleviation of the dysfunction in a shorter period of time than the case where only rehabilitation is performed.

Examples of nerve injury include stroke, brain injury, spinal cord injury, neurodegenerative diseases and demyelinating diseases, and preferable examples include stroke, brain injury and spinal cord injury.

Examples of stroke include brain infarction, brain thrombosis, brain embolism, atherothrombotic brain infarction, cardiogenic brain embolism, brain hemorrhage and subarachnoid hemorrhage.

The "brain injury" means a condition in which a part of the brain is injured, regardless of its cause. Examples of brain injury include traumatic brain injury, head trauma, brain contusion, acquired brain injury, brain tumor, brain tumor extirpation and encephalitis.

The "spinal cord injury" means a condition in which a part of the spinal cord is injured, regardless of its cause. Examples of causes of spinal cord injury include traffic accidents, falling from a high place, falling, bruising, being pinned under something heavy and sports.

Examples of neurodegenerative diseases include spinocerebellar ataxia, Parkinson's disease, amyotrophic lateral sclerosis, Huntington's disease, progressive supranuclear palsy and multiple system atrophy.

Examples of demyelinating diseases include multiple sclerosis, Guillain-Barre syndrome and chronic inflammatory demyelinating polyneuropathy.

The "motor dysfunction" means a condition in which voluntary movements are difficult, disabled or not smoothly performed, and means motor paralysis and ataxia. Specific examples include disturbances in skilled movements, Babinski's sign, spastic paralysis, spasticity (chronic phase), exaggerated deep tendon reflex (chronic phase), muscular rigidity, bradypragia, involuntary movements (for example, tremor, chorea, athetosis, and dystonia), ataxia (limbs/trunk), gait dysfunction and upper limb dysfunction attributed thereto, as well as language dysfunction and eating/swallowing disorders. Preferable examples include gait dysfunction and upper limb dysfunction.

The "sensory dysfunction" means a condition in which a cerebral disorder disables normal recognition of superficial sensation such as tactile sense, pressure sense and temperature sense, deep sensation such as position sense and vibration sense, as well as combined sensation such as two-point discrimination and graphesthesia. Specific examples include sensory extinction (loss), reduced sensation (decline), hyperesthesia and dysesthesia (paresthesia). The sensory dysfunction also includes sensory disorders caused by sites where sensory disorders such as a hemisensory disorder, a superficial sensation disorder and a whole sensation disorder are occurring.

The "language dysfunction" means aphasia involving a decreased ability in aspects of language such as listening to, reading, speaking and writing words, due to injury in an area controlling the language function; and dyskinetic dysarthria involving symptoms such as difficulty in phonation or articulation due to paralysis of phonic/speech organs such as the lip, tongue and vocal cords, as well as motor control disorders (ataxia). The language dysfunction preferably means dyskinetic dysarthria.

Examples of diseases against which the post-nerve injury rehabilitation effect-enhancing agent shows efficacy include stroke, brain injury, spinal cord injury, neurodegenerative diseases, and demyelinating diseases, and preferable examples include stroke, brain injury and spinal cord injury.

The alkyl ether derivative represented by the general formula [1] or a salt used in the present invention can be produced using any of or an appropriate combination of methods known per se, or using the method described in Patent Document 1.

The alkyl ether derivative represented by the general formula [1] or a salt thereof used in the present invention can be blended with various pharmaceutical additives such as excipients, binders, disintegrators, disintegration inhibitors, anti-caking/anti-sticking agents, lubricants, absorbing/adsorbing carriers, solvents, bulking agents, isotonic agents, solubilizers, emulsifiers, suspending agents, thickeners, coating agents, absorption enhancers, gelation/coagulation promoters, light stabilizers, preservatives, desiccants, emulsion/suspension/dispersion stabilizers, coloration preventing agents, deoxidizers/antioxidants, flavoring agents, coloring agents, whipping agents, antifoaming agents, soothing agents, antistatic agents and buffers/pH regulators, to be made into pharmaceutical preparations such as oral preparations (tablets, capsules, powders, granules, fine granules, pills, suspensions, emulsions, solutions, syrups and the like), injections and eye drops.

The above-described various drugs can be prepared using general methods.

Solid oral preparations such as tablets, powders and granules may be prepared in accordance with conventional methods, using pharmaceutical additives for solid preparations, for example, excipients such as lactose, sucrose, sodium chloride, glucose, starch, calcium carbonate, kaolin, crystalline cellulose, anhydrous dibasic calcium phosphate, partially pregelatinized starch, corn starch and alginic acid; binders such as simple syrup, glucose solution, starch solution, gelatin solution, polyvinyl alcohol, polyvinyl ether, polyvinylpyrrolidone, carboxymethylcellulose, shellac, methylcellulose, ethylcellulose, sodium alginate, gum arabic, hydroxypropylmethylcellulose, hydroxypropylcellulose, water and ethanol; disintegrators such as dry starch, alginic acid, agar powder, starch, cross-linked polyvinylpyrrolidone, cross-linked carboxymethylcellulose sodium, carboxymethylcellulose calcium and sodium starch glycolate; disintegration inhibitors such as stearyl alcohol, stearic acid, cocoa butter and hydrogenated oil; anti-caking/anti-sticking agents such as aluminum silicate, calcium hydrogen phosphate, magnesium oxide, talc and anhydrous silicic acid; lubricants such as carnauba wax, light anhydrous silicic acid, aluminum silicate, magnesium silicate, hardened oil, hardened vegetable oil derivatives, sesame oil, bleached beeswax, titanium oxide, dry aluminum hydroxide gel, stearic acid, calcium stearate, magnesium stearate, talc, calcium hydrogen phosphate, sodium lauryl sulfate and polyethylene glycol; absorption enhancers such as quaternary ammonium salts, sodium lauryl sulfate, urea and enzymes; and absorption/adsorption carriers such as starch, lactose, kaolin, bentonite, anhydrous silicic acid, hydrated silicon dioxide, magnesium aluminometasilicate and colloidal silicic acid.

Moreover, as required, tablets can be made into tablets having general coatings, for example, sugarcoated tablets, gelatin-coated tablets, gastric-coated tablets, enteric-coated tablets and water-soluble film-coated tablets.

Capsules are prepared by mixing with the above-listed various pharmaceuticals, and filling hard gelatin capsules, soft capsules and the like with the mixtures.

Aqueous or oily suspensions, solutions, syrups and elixirs can be also prepared in accordance with conventional methods, using the above-described various additives for liquid preparations, such as solvents, bulking agents, isotonic agents, solubilizers, emulsifiers, suspending agents and thickeners.

Injections may be prepared in accordance with conventional methods, using pharmaceutical additives for liquid preparations, for example, diluents such as water, ethyl alcohol, Macrogol, propylene glycol, citric acid, acetic acid, phosphoric acid, lactic acid, sodium lactate, sulfuric acid and sodium hydroxide; pH regulators and buffers such as sodium citrate, sodium acetate and sodium phosphate; stabilizers such as sodium pyrosulfite, ethylenediamine tetraacetic acid, thioglycolic acid and thiolactic acid; isotonic agents such as salt, glucose, mannitol and glycerol; solubilizers such as carboxymethylcellulose sodium, propylene glycol, sodium benzoate, benzyl benzoate, urethane, ethanol amine and glycerol; soothing agents such as calcium gluconate, chlorobutanol, glucose and benzyl alcohol; and local anesthetics.

Eye drops may be prepared in accordance with conventional methods, by blending as appropriate, preservatives such as chlorobutanol, sodium dehydroacetate, benzalkonium chloride, cetylpyridinium chloride, phenethyl alcohol, methyl parahydroxybenzoate and benzethonium chloride; buffers such as borax, boric acid and potassium dihydrogen phosphate; thickeners such as methylcellulose, hydroxyethylcellulose, carboxymethylcellulose, hydroxypropylmethylcellulose, polyvinyl alcohol, carboxymethylcellulose sodium and chondroitin sulfate; solubilizers such as polysorbate 80 and polyoxyethylene hardened castor oil 60; stabilizers such as disodium edetate and sodium bisulfite; and isotonic agents such as sodium chloride, potassium chloride and glycerol.

While the method of administering the above-described preparations is not particularly limited, it is determined as appropriate, depending on the dosage form, the patient's age, sex and other conditions, as well as the severity of the patient's condition.

While the dose of the active ingredient of the above-described preparations is selected as appropriate, depending on, for example, the use, the patient's age, sex, disease form and other conditions, 0.1 to 1000 mg per day of the active ingredient may be generally administered to an adult in single or divided doses, and preferably, 40 to 500 mg per day of the active ingredient may be administered in single or divided doses.

Next, the present invention will be described based on test examples and preparation examples, which are not intended to limit the present invention.

A maleate salt of 1-(3-(2-(1-benzothiophen-5-yl)ethoxy)propyl)azetidin-3-ol (hereinafter referred to as Compound A) was used as a test compound.

Test Example 1

Action of enhancing the recovery effect obtained by training the forelimb function lost after freezing damage-induced brain injury was examined.

A test was performed using the following method, by referring to the method described in Journal of Neuroscience Methods, Vol. 193, Issue 1, Pages 82-85 (2010) and Nature, Vol. 462, Issue 7275, Pages 915-919 (2009).

Six-week-old male C57BL/6J mice (Charles River Japan) were used in the test. The mice were raised in an environment in which they had free access to feed and water, under a light-dark cycle of 12 hours (light period: 7:00-19:00, dark period: 19:00-7:00).

The test was performed for groups organized as shown in Table 1. The mice were randomly assigned to the groups.

TABLE 1

Figure 1:
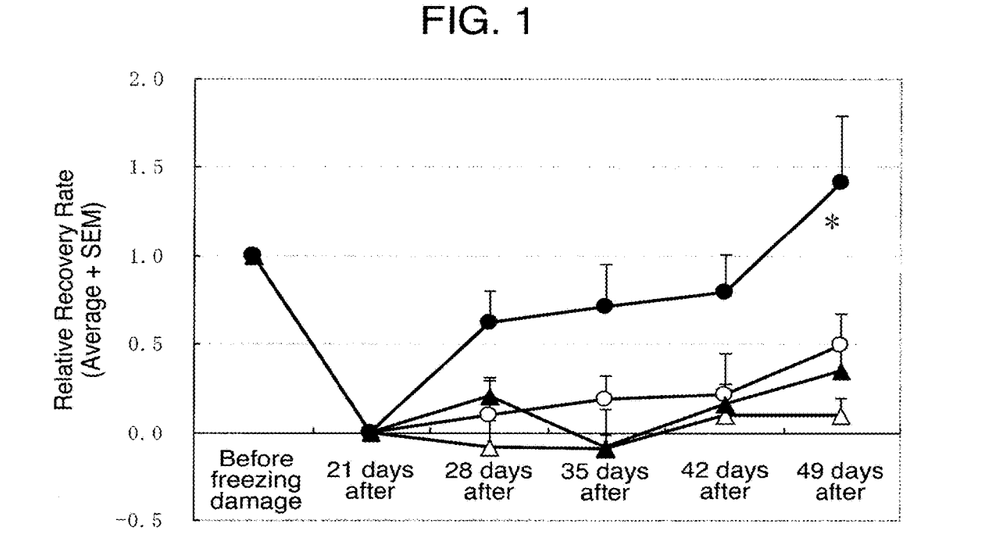
FIG. 1 is a diagram showing a comparison of post-nerve injury rehabilitation effects. The vertical axis represents a relative recovery rate (expressed as the average value±SEM) when the success rate on the final day of motor learning is defined as 1, and the success rate 21 days after freezing damage is defined as 0. The horizontal axis represents, from the left, the final day of motor learning (before the freezing damage), 21 days, 28 days, 35 days, 42 days and 49 days after the freezing damage. * represents the presence of a significant difference (p<0.05) in comparison with a control group (Δ).

| Test Compound | Administration Route/ Times | Dose | Training | Number of Mice | Legends in FIG. 1 |
|---|---|---|---|---|---|
| — | Oral/Twice a day | — | No | 6 | Δ |
| Compound A | Oral/Twice a day | 30 mg/kg/time | No | 7 | ○ |
| — | | — | Yes (30 min/day) | 11 | ▲ |
| Compound A | | 30 mg/kg/time | Yes (30 min/day) | 11 | ● |

An acrylic rectangular enclosure (length×width×height; 15×8.5×20 cm) in which only the front face of the four faces was transparent, and the other three faces were black was used. A slit measuring 0.5 cm in width×13 cm in height was formed on the right side of the front face when seen from the front. A transparent acrylic plate measuring 8.5 cm in width×1.25 cm in height was used as the feed plate. Diced almonds (K's Factory, Co., Ltd.) were used as the feed for use in the evaluation.

In order to allow the mice to acclimate to the test environment, the mice were left in a behavioral test chamber for about 1 hour before an acclimation procedure. Moreover, in order to reduce the alertness of the mice to the testing apparatus, a pinch of bedding from the home cage was spread within the testing apparatus.

In order to allow the mice to acclimate to the testing apparatus, the acclimation procedure was performed for 4 days. Specifically, on day 1, the mice were placed within the testing apparatus and allowed to explore freely for 10 minutes. After the acclimation procedure on day 1, the mice were subjected to feed restriction (1.5 g/mouse) using feed composed of a mixture of diced almonds and crushed normal feed. Thereafter, the feed restriction was applied until the acclimation procedure was completed. On day 2, a pinch of diced almonds were placed in the position of the slit within the testing apparatus, and then the mice were placed within the testing apparatus and allowed to explore freely for 10 minutes. On day 3, in addition to the same position as that on day 2, a pinch of diced almonds were placed in the position of the slit in the feed plate located outside the testing apparatus, and then the mice were placed within the testing apparatus and allowed to explore freely for 10 minutes. On day 4, a pinch of diced almonds were placed only in the position of the slit in the feed plate located outside the testing apparatus, and then the mice were placed within the testing apparatus and allowed to explore freely for 10 minutes.

In order to allow the mice to learn to take the diced almonds with the left forelimb from the feed plate located outside the testing apparatus, a motor learning procedure was performed for 4 days. From the day before the beginning of the learning, the mice were subjected to the feed restriction as in the acclimation procedure. Moreover, as in the acclimation procedure, in order to allow the mice to acclimate to the test environment, the mice were left in a behavioral test chamber for about 1 hour before the learning procedure. Furthermore, in order to reduce the alertness of the mice to the testing apparatus, a pinch of bedding from the home cage was spread within the testing apparatus.

The motor learning was performed by placing one of diced almonds on the extended line of a left end of the slit, and evaluating the method of taking the feed. The position of this feed was where the mice could not touch the feed with the right forelimb. The number of trials per day was 30. The test duration was 20 minutes at maximum, and the trials on that day were terminated when 20 minutes had passed from the beginning of the test, even if the number of trials did not reach 30.

A case where a mouse was able to extend the left forelimb through the slit, and carry the diced almond into the mouth without dropping it was determined to be successful. A case where a mouse flicked the diced almond, a case where a mouse dropped the diced almond before carrying it into the mouth, a case where a mouse extended the forelimb through the slit without touching the diced almond, or a case where a mouse took the diced almond with the tongue was determined to be a failure. The ratio of the number of successful trials with respect to the total number of trials was calculated as the success rate, and only the individuals having a success rate over 25% on day 4 were used for the following test.

An ophthalmic cryosurgery unit (Keeler Cryomatic: M-4000; Keeler & Y. Na, Ltd.) was used as the apparatus for injuring the cerebral cortex.

Only the individuals having a success rate over 25% on the final day of motor learning were injured.

Each of the mice was generally anesthetized with isoflurane. The anesthetized mouse was fixed onto a brain stereotaxic apparatus, and an incision was made in the scalp along the midline to expose the parietal bones. A line in parallel with the midline was drawn with a skin marker in a position 1.0 mm toward the right side of the head from the bregma. Next, a line orthogonal to the midline was drawn with the skin marker in a position 1.0 mm toward the back of the head from the bregma. The parietal bones were circularly removed with an electric trephine (diameter: 2.0 mm) in a position touching these two lines. After the removal of the parietal bones, a cooled probe (diameter: 2.5 mm) for retinal detachment was directly applied to the brain surface twice, each for 30 seconds, to induce freezing damage. After the completion of the freezing damage, the scalp was sutured, and the mouse was allowed to recover from anesthesia. After the recovery, the mouse was lifted with the tail being held, and paralysis of the left forelimb and bending of the body were examined to confirm whether the brain injury was successfully induced or not.

From the day following the freezing damage to 49 days after the freezing damage, the test compound was orally administered twice a day, at an interval of 6 hours or longer. The mice were randomly assigned to groups. A solution of Compound A (3 mg/mL) dissolved in distilled water was prepared as the solution to be administered. The dose of the solution of Compound A was 10 mL/kg. Distilled water was administered into a control group.

For training, under the same conditions as those used on day 4 of the acclimation procedure, a pinch of diced almonds were placed in the position of the slit in the feed plate located outside the testing apparatus, and then the mice were placed within the testing apparatus and allowed to explore freely for 30 minutes. The training was carried out every day between 22 days and 48 days after the freezing damage, excluding the days on which a forelimb function evaluation was performed.

The forelimb function evaluation was carried out 21 days, 28 days, 35 days, 42 days and 49 days after the freezing damage. The mice were subjected to feed restriction (1.5 g/mouse) on the day before the evaluation was carried out. Moreover, in order to allow the mice to acclimate to the test environment, the mice were left in a behavioral test chamber for about 1 hour before the test was carried out. Furthermore, in order to reduce the alertness of the mice to the testing apparatus, a pinch of bedding from the home cage was spread within the testing apparatus. The success rate was calculated using the same method as that in the motor learning. A relative recovery rate was determined with the success rate on the final day of motor learning (before the freezing damage) being defined as 1, and the success rate 21 days after the freezing damage being defined as 0. The results are shown in FIG. 1.

The Compound A-administered and trained group (●) showed a much higher relative recovery rate within a short period, compared to the other groups (Δ, ○ and ▲) (FIG. 1).

Test Example 2

Action of enhancing the recovery effect obtained by training the forelimb function lost after internal capsule hemorrhage-induced brain injury was examined, using internal capsule hemorrhage mouse models.

A test was carried out using the following method, by referring to Plos One, Vol. 8, e67691 (2013) and Behav Brain Res., Vol. 20, Issue 225, Pages 126-34 (2011).

Six-week-old male C57BL/6J mice (Charles River Japan) were used in the test. The mice were raised in an environment in which they had free access to feed and water, under a light-dark cycle of 12 hours (light period: 7:00-19:00, dark period: 19:00-7:00).

The test was performed for groups organized as shown in Table 2. The mice were randomly assigned to the groups.

TABLE 2

Figure 2:
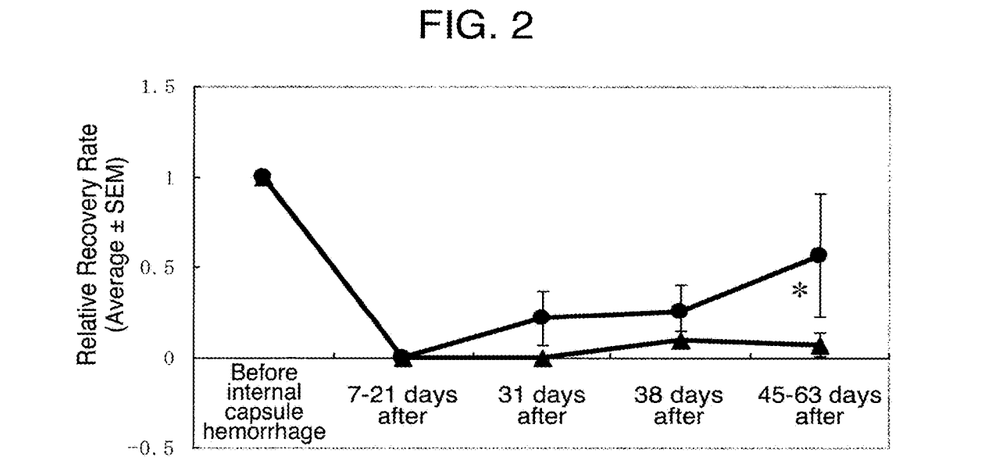
FIG. 2 is a diagram showing a comparison of post-nerve injury rehabilitation effects. The vertical axis represents a relative recovery rate (expressed as the average value±SEM) when the success rate on the final day of motor learning is defined as 1, and the average value of success rates 7 days, 14 days and 21 days after the induction of internal capsule hemorrhage is defined as 0. The horizontal axis represents, from the left, the final day of motor learning (before the internal capsule hemorrhage), 7 to 21 days, 31 days, 38 days and 45 to 63 days after the induction of the internal capsule hemorrhage. * represents the presence of a significant difference (p<0.05) in comparison with a control group (▲).

| Test Compound | Administration Route/Times | Dose | Training | Number of Mice | Legends in FIG. 2 |
| --- | --- | --- | --- | --- | --- |
| — | Oral/Once a day | — | Yes (30 min/day) | 6 | ▲ |
| Compound A | | 20 mg/kg/time | Yes (30 min/day) | 6 | ● |

An acrylic rectangular enclosure (length×width×height; 15×8.5×20 cm) in which only the front face of the four faces was transparent, and the other three faces were black was used. A slit measuring 0.5 cm in width×13 cm in height was formed on the right side of the front face when seen from the front. A transparent acrylic plate measuring 8.5 cm in width×1.25 cm in height was used as the feed plate. Diced almonds (K's Factory, Co., Ltd.) were used as the feed for use in the evaluation.

In order to allow the mice to acclimate to the test environment, the mice were left in a behavioral test chamber for about 1 hour before an acclimation procedure. Moreover, in order to reduce the alertness of the mice to the testing apparatus, a pinch of bedding from the home cage was spread within the testing apparatus.

In order to allow the mice to acclimate to the testing apparatus, the acclimation procedure was performed for 4 days. Specifically, on day 1, the mice were placed within the testing apparatus and allowed to explore freely for 10 minutes. After the acclimation procedure on day 1, the mice were subjected to feed restriction (1.5 g/mouse) using feed composed of a mixture of diced almonds and crushed normal feed. Thereafter, the feed restriction was applied until the acclimation procedure was completed. On day 2, a pinch of diced almonds were placed in the position of the slit within the testing apparatus, and then the mice were placed within the testing apparatus and allowed to explore freely for 10 minutes. On day 3, in addition to the same position as that on day 2, a pinch of diced almonds were placed in the position of the slit in the feed plate located outside the testing apparatus, and then the mice were placed within the testing apparatus and allowed to explore freely for 10 minutes. On day 4, a pinch of diced almonds were placed only in the position of the slit in the feed plate located outside the testing apparatus, and then the mice were placed within the testing apparatus and allowed to explore freely for 10 minutes.

In order to allow the mice to learn to take the diced almonds with the left forelimb from the feed plate located outside the testing apparatus, a motor learning procedure was performed for 4 days. From the day before the beginning of the learning, the mice were subjected to the feed restriction as in the acclimation procedure. Moreover, as in the acclimation procedure, in order to allow the mice to acclimate to the test environment, the mice were left in a behavioral test chamber for about 1 hour before the learning procedure. Furthermore, in order to reduce the alertness of the mice to the testing apparatus, a pinch of bedding from the home cage was spread within the testing apparatus.

The motor learning was performed by placing one of diced almonds on the extended line of a left end of the slit, and evaluating the method of taking the feed. The position of this feed was where the mice could not touch the feed with the right forelimb. The number of trials per day was 30. The test duration was 20 minutes at maximum, and the trials on that day were terminated when 20 minutes had passed from the beginning of the test, even if the number of trials did not reach 30.

A case where a mouse was able to extend the left forelimb through the slit, and carry the diced almond into the mouth without dropping it was determined to be successful. A case where a mouse flicked the diced almond, a case where a mouse dropped the diced almond before carrying it into the mouth, a case where a mouse extended a forelimb through the slit without touching the diced almond, or a case where a mouse took the diced almond with the tongue was determined to be a failure. The ratio of the number of successful trials with respect to the total number of trials was calculated as the success rate, and only the individuals having a success rate over 25% on day 4 were used for the following test.

Collagenase (Collagenase IV-S, Sigma Aldrich, C5138) was used to induce hemorrhage from the internal capsule.

Only the individuals having a success rate over 25% on the final day of motor learning were injured.

Each of the mice was generally anesthetized with isoflurane. The anesthetized mouse was fixed onto a brain stereotaxic apparatus, and an incision was made in the scalp along the midline to expose the parietal bones. A position 2.2 mm toward the right side of the head from the bregma and a position 1.0 mm toward the back of the head from the bregma were marked with a skin marker. The parietal bones were circularly removed around the marked spots with an electric trephine (diameter: 2.3 mm). A microsyringe (35 gage) was inserted to a depth of 3.5 mm into the center of the site from which the parietal bones were removed, and left for 5 minutes, and then a total amount of 0.5 µL of collagenase (Collagenase IV-S, Sigma Aldrich, C5138) dissolved in physiological saline and diluted to a concentration of 0.03 mg/mL was injected at a flow rate of 0.1 µL per minute. After the injection, the microsyringe was left for 7 minutes, and then withdrawn. After the withdrawal, the scalp was sutured, and the mouse was allowed to recover from anesthesia. For the individual immediately after the induction of internal capsule hemorrhage, feed softened with moisture was placed near the animal to facilitate the intake of feed and water.

The forelimb motor function was evaluated 7, 14 and 21 days after the induction of the internal capsule hemorrhage, using the same method as that in the motor learning, and the average value of success rates was determined as the outcome of the motor function after the internal capsule hemorrhage.

After the completion of the evaluation 21 days after the induction of the internal capsule hemorrhage, the test compound was orally administered once a day. The mice were randomly assigned to groups. A solution of Compound A (2 mg/mL) dissolved in distilled water was prepared as the solution to be administered. The dose of the solution of Compound A was 10 mL/kg. Distilled water was administered into a control group.

Training was performed every day from 3 days after the initial administration of the test compound. For training, a pinch of diced almonds were placed in the position of the slit in the feed plate located outside the testing apparatus, and the mice were allowed to explore freely for 30 minutes. The training was performed after 1 hour from the administration of the test compound.

The forelimb motor function was evaluated, 31, 38, 45, 52, 59 and 63 days after the induction of the internal capsule hemorrhage, using the same evaluation method as that in the motor learning, and the success rate was calculated. A relative recovery rate was determined with the success rate on the final day of motor learning (before the internal capsule hemorrhage) being defined as 1, and the average value of success rates after 7, 14 and 21 days (7 to 21 days) from the induction of the internal capsule hemorrhage being defined as 0. As the success rate after 45 to 63 days, the average value after 45, 52, 59 and 63 days was used. The results are shown in FIG. 2.

The Compound A-administered and trained group (○) showed a much higher relative recovery rate, compared to the control group (▲) (FIG. 2).

Test Example 3 Action of enhancing the recovery effect obtained with rehabilitation-like training of the upper limb function lost after brain injury was examined, using internal capsule hemorrhage cynomolgus monkey models.

Two male cynomolgus monkeys (Tsukuba Primate Research Center, National Institute of Biomedical Innovation) were used in the test. The cynomolgus monkeys were raised in a breeding cage for old world monkeys (length×width×height; 79×47×80 cm) in which they had free access to feed and water, under a light-dark cycle of 12 hours (light period: 7:00-19:00 dark period: 19:00-7:00).

Motor learning and an upper limb function evaluation were performed by making the cynomolgus monkeys take feed provided in front of the breeding cage. A 3.5- or 7 mm square piece of apple was used as the feed for use in the evaluation.

In order to allow the cynomolgus monkeys to acclimate to the testing apparatus, and determine the dominant hand of each of the individuals, a 7 mm square piece of apple attached to a needle tip was provided in the center of the front face of the cage, and the behavior of the cynomolgus monkey taking the feed was observed. The hand more often used in a total of 150 trials (30 trials a day for 5 days) was determined as its dominant hand.

In order to allow the cynomolgus monkeys to learn to take the provided feed with their dominant hand, a motor learning procedure was performed 5 days a week for 4 weeks (for a total of 20 days). The motor learning was performed using the following six tasks for use in the upper limb function evaluation and the rehabilitation-like training. On the days of learning, the cynomolgus monkeys carried out the tasks in the fasted state.

Figure 3:
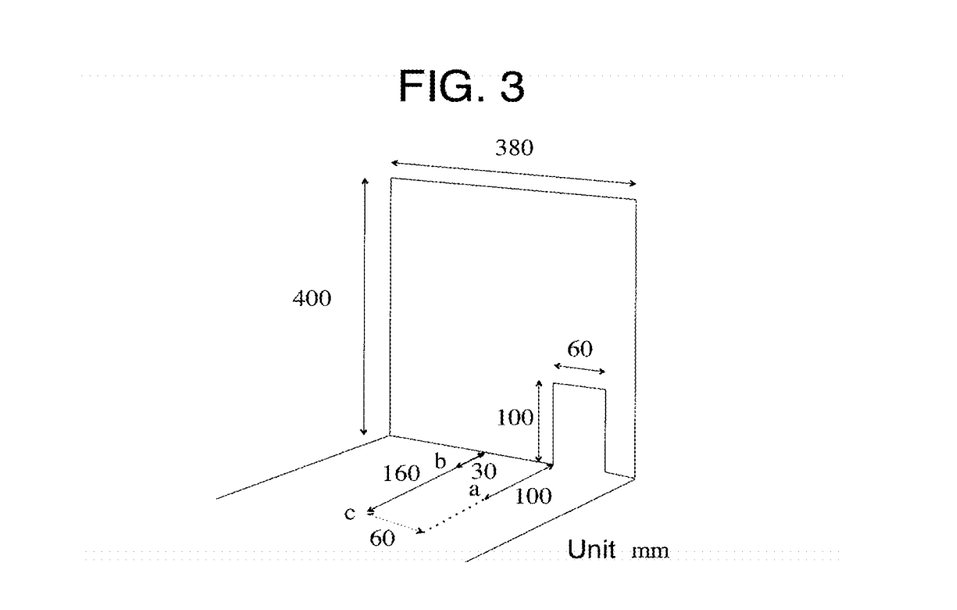
FIG. 3 is a diagram showing a board with a slit used as a testing apparatus.
Figure 4:
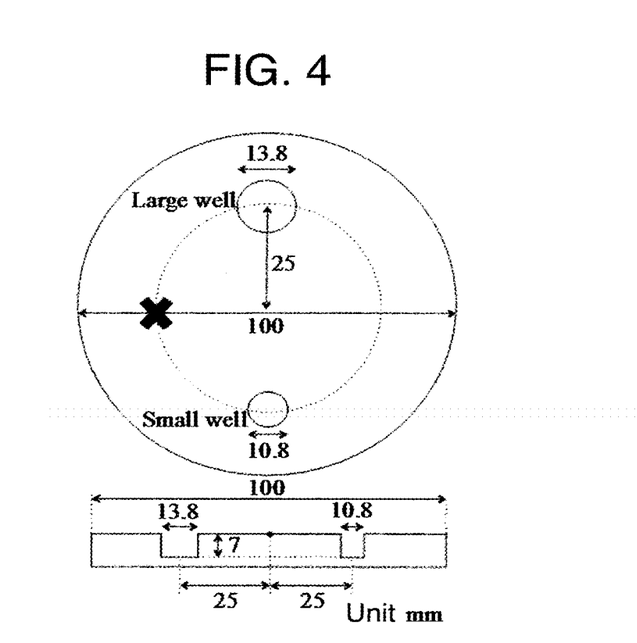
FIG. 4 is a diagram showing a Kluver board used as a testing apparatus. The upper diagram (circle) shows a plan view. The lower diagram (rectangle) shows a cross-sectional view seen from a left-side direction.

Task A: The apparatus shown in FIG. 3 was installed on the front face of the breeding cage, and the Kluver board shown in FIG. 4 was installed right in front of the slit in the apparatus. The position where the feed was provided on the Kluver board was the position nearest to the slit. The behavior of the cynomolgus monkey extending its hand through the slit to take the feed from a hole opened in the Kluver board was observed. A 3.5 mm square piece of apple was used as the feed for use in the evaluation. Trials were carried out 20 times each in the order of a place without a hole (the cross mark in FIG. 4), the Large well and the Small well.

Task B: The testing apparatus shown in FIG. 3 (for the left-handed in FIG. 3) was installed on the front face of the breeding cage, and the behavior of the cynomolgus monkey extending its hand through the slit in the apparatus to take the feed placed in positions a, b and c shown in FIG. 3 was observed. A 7 mm square piece of apple was used as the feed for use in the evaluation. Twenty trials in each of the positions, i.e., a total of 60 trials, were carried out.

Figure 5:
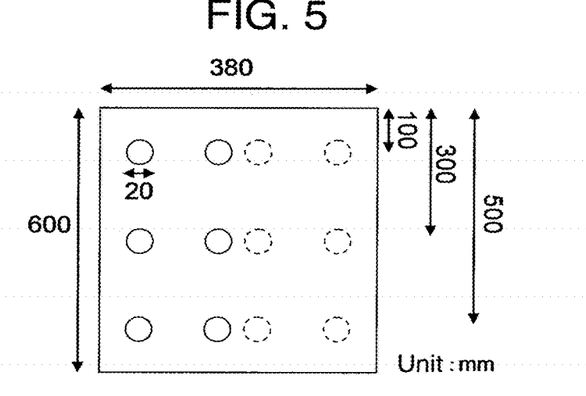
FIG. 5 is a diagram showing a board with holes used as a testing apparatus.

Task C: The apparatus shown in FIG. 5 was installed on the front face of the breeding cage, and a 7 mm square piece of apple attached to a needle tip was horizontally provided through a hole opened in the apparatus. The six holes shown by the solid circles in FIG. 5 were used for the right-handed, and the six holes shown by the dotted circles in FIG. 5 were used for the left-handed. A 7 mm square piece of apple was used as the feed for use in the evaluation. The behavior of the cynomolgus monkey taking the feed from the holes was observed. Ten trials in each of the holes, i.e., a total of 60 trials, were carried out.

Task D: A 7 mm square piece of apple attached to a needle tip was horizontally provided from the front face of the breeding cage. The behavior of the cynomolgus monkey taking the feed was observed. A total of 30 trials were performed.

Figure 6:
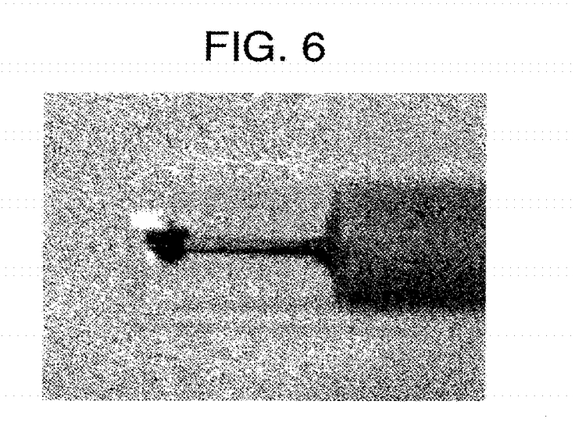
FIG. 6 shows a photograph taken when a 7 mm square piece of apple attached to a needle tip through an acrylic pipe was horizontally provided.

Task E1: A 7 mm square piece of apple attached to a needle tip through an acrylic pipe was horizontally provided, as shown in FIG. 6. The behavior of the cynomolgus monkey taking the feed from the acrylic pipe was observed. A total of 30 trials were performed.

Figure 7:
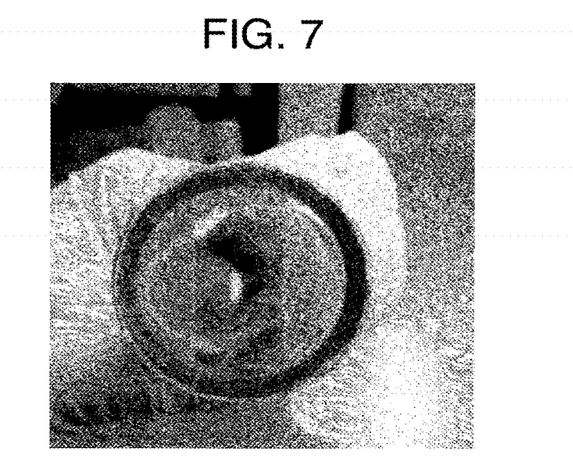
FIG. 7 is a photograph taken when an acrylic pipe in which a slit was formed at its tip was made to face forward.

Task E2: A slit was formed at a tip of an acrylic pipe of the same type as that used in E1, as shown in FIG. 7, and a 7 mm square piece of apple attached to a needle tip was provided as in the task E1. The behavior of the cynomolgus monkey taking the feed through the slit in the acrylic pipe was observed. A total of 30 trials were performed.

A case where the cynomolgus monkey drew the feed into the cage with its dominant hand without dropping it in a single trial was determined to be successful. A case where the cynomolgus monkey used its non-dominant hand, or could not take the feed even after being provided for 10 seconds was determined to be a failure. Where the cynomolgus monkey could not take the feed even though 10 seconds had passed after the feed was provided, the feed was replaced with fresh feed before proceeding to a subsequent trial. The average value of success rates during the final two days (the ratio of successful trials with respect to the total number of trials) was determined as the outcome of the motor learning.

Internal capsule hemorrhage-induced brain injury was inflicted on the individuals that had completed the motor learning.

MRI was conducted on the day before the internal capsule hemorrhage models were prepared. The MRI was conducted by tranquilizing the cynomolgus monkey through intramuscular injection of ketamine hydrochloride and atropine sulfate, followed by passage of a tube into the trachea, and fixing the head with a stereo unit while observing vital signs (blood pressure, oxygen saturation and pulse) under inhalation anesthesia with isoflurane.

Collagenase (Collagenase IV-S, Sigma Aldrich, C5138) was used to induce hemorrhage from the internal capsule.

By conducting MRI for navigation and referring to a T1-weighted image, the posterior limb of the internal capsule contralateral to the dominant hand was identified. A skin incision with a diameter of approximately 3 cm was made in the top of the head. From craniotomy until the identification of the dura mater, mannitol was administered through the jugular vein. A site of the skull for insertion of a microsyringe was drilled to remove a portion of the skull measuring approximately 10 mm in the anteroposterior direction and 5 mm in width. The administration of mannitol was completed, and the microsyringe was inserted to inject 3 μL of 200 U/L collagenase while the position and the depth were being observed with the navigation system from above the exposed dura mater. The center was defined as being 3 mm posterior to the tip of the central sulcus and immediately above the upper part of the inner side of the putamen, and the collagenase was injected at 9 points in the anteroposterior and vertical directions with respect to the center. After the injection, Francetin was applied over the dura mater, and the fascia and the skin were sutured.

One day, 3 to 5 days, 7 days and 14 days after the induction of the internal capsule hemorrhage, MRI was conducted, and the injured volume of the brain caused by the internal capsule hemorrhage was estimated to confirm that there was no significant difference in injured volume.

One to 14 days after the induction of the internal capsule hemorrhage, until the use of the paralyzed upper limb was observed, while free behavior of the cynomolgus monkey within the cage was being observed, the cynomolgus monkey was made to perform passive bending/extension and grasping movements, each for 15 minutes, in order to prevent disuse of the paralyzed upper limb.

One of the two male injured cynomolgus monkeys underwent the administration of Compound A and the rehabilitation-like training. The other cynomolgus monkey did not undergo any administration of Compound A, but the course of spontaneous recovery after the induction of the internal capsule hemorrhage and recovery through the rehabilitation-like training were observed.

The test was performed for groups organized as shown in Table 3.

TABLE 3

| Test Compound | Administration Route/Times | Solvent | Dose | Training | Number of Monkeys |
|---|---|---|---|---|---|
| — | Intramuscular/Once a day | Otsuka Glucose Injection 5% | — | Yes | 1 |
| Compound A | Intramuscular/Once a day | Otsuka Glucose Injection 5% | 3 mg/kg/time | Yes | 1 |

A 7 mm square piece of apple attached to a needle tip was provided from the front face of the cage, and it was observed whether the cynomolgus monkey was able to voluntarily reach the apple. From the day following the day on which the voluntary reach with the paralyzed upper limb was observed, feed was provided in the place without a hole on the Kluver board (FIG. 4), and it was observed whether the cynomolgus monkey was able to voluntarily reach the feed with the paralyzed upper limb. The day on which the voluntary reach to the Kluver board with the paralyzed upper limb was observed was defined as day 0 of the use of the paralyzed upper limb, and from the following day (after one day from the use of the paralyzed upper limb), an upper limb motor function evaluation, the administration of Compound A and the rehabilitation-like training were carried out.

Every day in the morning after one day from the first use of the paralyzed upper limb, the same tasks as those in the motor learning described above were carried out as the upper limb function evaluation. A video for evaluating whether each trial was successful or not was recorded using a digital video camera.

From one day after the first use of the paralyzed upper limb to the completion of the test, Compound A was intramuscularly administered once a day every day in the afternoon, after the upper limb motor function evaluation. A solution of Compound A (15 mg/mL) dissolved in Otsuka Glucose Injection 5% was used as the solution to be administered, and the dose thereof was 0.2 mL/kg.

In the rehabilitation-like training, the same tasks as those in the motor learning described above were carried out every day until the completion of the evaluation, from the day following the day on which the cynomolgus monkey was able to voluntarily reach the task apparatus. The Compound A-administered individual underwent the rehabilitation-like training within 2 hours after the administration.

From the recorded video, the movements of the hand taking the feed were observed in detail, and evaluation was made as to whether each trial was successful or not.

After the brain injury, a remarkable tendency to recovery was observed in the individual wherein the administration of Compound A and the rehabilitation-like training were carried out. Moreover, in this individual, accurate grasping similar to that before the brain injury was observed after the beginning of the rehabilitation-like training. In the individual wherein any administration of Compound A was not carried out, the post-disorder recovery was limited even after the rehabilitation-like training was started, and accurate grasping was not observed.

Preparation Example 1

A mixture of 50 mg of Compound A, 60 mg of lactose, 60 mg of Ceolus® PH-302 (manufactured by Asahi Kasei Chemicals Corporation), 4 mg of Kollidon® CL (manufactured by BASF Corporation) and 1 mg of magnesium stearate was mixed and made into round tablets with a diameter of 7 mm, each having a weight of 175 mg, to obtain the tablets containing 50 mg of Compound A.

Preparation Example 2

A mixture of 50 mg of Compound A, 60 mg of D-mannitol, 39 mg of Starch 1500 (manufactured by Colorcon Corporation) and 1 mg of magnesium stearate was mixed, and #4 gelatin capsules were filled with 150 mg of the resultant per capsule to obtain the capsules.

The invention claimed is:

1. A method for enhancing recovery from or alleviation of functional disorder, comprising:
    administering to a patient having a nerve injury and undergoing rehabilitation 1-(3-(2-(1-benzothiophen-5-yl)ethoxy)propyl)azetidin-3-ol or a salt thereof such that the rehabilitation and 1-(3-(2-(1-benzothiophen-5-yl)ethoxy)propyl)azetidin-3-ol or the salt exhibit a synergistic effect or a statistically significant effect.

2. The method of claim 1, wherein the salt of 1-(3-(2-(1-benzothiophen-5-yl)ethoxy)propyl)azetidin-3-ol is a salt with a mineral acid, a salt with an organic carboxylic acid, a salt with a sulfonic acid, a salt with an alkali metal, a salt with an alkaline earth metal, an ammonium salt, or a salt with a nitrogen-containing organic base.

3. The method of claim 1, wherein 1-(3-(2-(1-benzothiophen-5-yl)ethoxy)propyl)azetidin-3-ol or the salt is administered to the patient such that the patient exhibits statistically significant recovery from the functional disorder as compared to a patient undergoing the rehabilitation and not administered with 1-(3-(2-(1-benzothiophen-5-yl)ethoxy)propyl)azetidin-3-ol or the salt, and a patient administered with 1-(3-(2-(1-benzothiophen-5-yl)ethoxy)propyl)azetidin-3-ol or the salt and not undergoing the rehabilitation.

4. The method of claim 1, wherein the functional disorder is motor dysfunction.

5. The method of claim 4, wherein the motor dysfunction is at least one selected from the group consisting of a disturbances in skilled movements, Babinski's sign, spastic paralysis, chronic phase spasticity, chronic phase exaggerated deep tendon reflex, muscular rigidity, bradypragia, tremor, chorea, athetosis, dystonia, ataxia, gait dysfunction, upper limb dysfunction, language dysfunction, an eating disorder, and a swallowing disorder.

6. The method of claim 4, wherein the motor dysfunction is at least one selected from the group consisting of gait dysfunction and upper limb dysfunction.

7. The method of claim 1, wherein the nerve injury is at least one selected from the group consisting of a stroke, a brain injury, a spinal cord injury, a neurodegenerative disease, and a demyelinating disease.

8. The method of claim 1, wherein the nerve injury is at least one selected from the group consisting of a stroke, a brain injury, and a spinal cord injury.

9. The method of claim 1, wherein the rehabilitation includes motor dysfunction recovery training.

10. The method of claim 1, wherein 1-(3-(2-(1-benzothiophen-5-yl)ethoxy)propyl)azetidin-3-ol or the salt is administered to the patient for at least 28 days.

11. The method of claim 1, wherein 1-(3-(2-(1-benzothiophen-5-yl)ethoxy)propyl)azetidin-3-ol or the salt is administered to the patient for at least 49 days.

12. The method of claim 1, wherein the patient is an adult human and 1-(3-(2-(1-benzothiophen-5-yl)ethoxy)propyl)azetidin-3-ol or the salt is administered to the patient in an amount of from 0.1 to 1,000 mg per day in a single dose or divided doses.

13. The method of claim 1, wherein the patient is an adult human and 1-(3-(2-(1-benzothiophen-5-yl)ethoxy)propyl)azetidin-3-ol or the salt is administered to the patient in an amount of from 40 to 500 mg per day in a single dose or divided doses.

* * * * *